US011185542B2

(12) United States Patent
Pan et al.

(10) Patent No.: US 11,185,542 B2
(45) Date of Patent: Nov. 30, 2021

(54) USES OF DOPAMINE BETA-HYDROXYLASE (DBH) INHIBITORS AND SEROTONIN RECEPTOR (5-HT) ANTAGONISTS FOR THE TREATMENT OF CANCER (71) Applicant: Jiangsu Yahong Meditech Co., Ltd., Taizhou Jiangsu (CN)

(72) Inventors: Ke Pan, Chadds Ford, PA (US); Qiang Li, Shanghai (CN)

(73) Assignee: Jiangsu Yahong Meditech Co., Ltd., Jiangsu (CN)

( * ) Notice: Subject to any disclaimer, the term of this patent is extended or adjusted under 35 U.S.C. 154(b) by 0 days.

(21) Appl. No.: 16/319,859

(22) PCT Filed: Jul. 27, 2017

(86) PCT No.: PCT/US2017/044068
§ 371 (c)(1),
(2) Date: Jan. 23, 2019

(87) PCT Pub. No.: WO2018/022823
PCT Pub. Date: Feb. 1, 2018

(65) Prior Publication Data
US 2019/0269673 A1 Sep. 5, 2019

Related U.S. Application Data (60) Provisional application No. 62/367,728, filed on Jul. 28, 2016.

(51) Int. Cl.
*A61P 35/00* (2006.01)
*A61K 31/417* (2006.01)
*A61K 31/4178* (2006.01)
*A61K 31/495* (2006.01)

(52) U.S. Cl.
CPC ............ *A61K 31/495* (2013.01); *A61P 35/00* (2018.01); *A61K 31/417* (2013.01); *A61K 31/4178* (2013.01)

(58) Field of Classification Search
CPC .. A61K 31/17; A61K 31/4164; A61K 31/417; A61P 35/00
See application file for complete search history.

(56) References Cited

U.S. PATENT DOCUMENTS 5,538,988 A * 7/1996 Martinez .............. C07D 403/04
514/384
2013/0261074 A1 10/2013 Bhatia et al.

FOREIGN PATENT DOCUMENTS

| WO | WO-0160349 A2 * | 8/2001 | ............ A61P 35/00 |
| WO | 2009016488 A2 | 2/2009 | |
| WO | 2009055001 A2 | 4/2009 | |
| WO | WO-2009055001 A2 * | 4/2009 | ............ A61K 31/55 |
| WO | 2015158890 A1 | 10/2015 | |
| WO | 2015197839 A1 | 12/2015 | |

OTHER PUBLICATIONS

Almeida et al., "Etamicastat, a novel dopamine B-hydroxylase inhibitor: tolerability, pharmacokinetics, and pharmacodynamics in patients with hypertension," Clin. Ther., vol. 35, No. 12, pp. 1983-1996 (2013).
Axelsson et al., "Effects of amperozide in schizophrenia. An open study of a potent 5-HT2 receptor antagonist," Psychopharmacology (Berlin), vol. 104, No. 3, pp. 287-292 (1991).
Beliaev et al., "Synthesis and biological evaluation of novel, peripherally selective chromanylimidazolethione-based inhibitors of dopamine beta-hydroxylase," J. Med. Chem., vol. 49, No. 3, pp. 1191-1197 (2006).
Bhaduri et al., "Analysis of polymorphisms in the dopamine beta hydroxylase gene: association with attention deficit hyperactivity disorder in Indian children," Indian Pediatrics, vol. 42, No. 2, pp. 123-129 (2005).
Combarros et al., "The dopamine B-hydroxylase-1021C/T polymorphism is associated with the risk of Alzheimer's disease in the Epistasis Project," BMC Medical Genetics, vol. 11, No. 162, pp. 1-10 (2010).
Cubells et al., "Linkage analysis of plasma dopamine B-hydroxylase activity in families of patients with schizophrenia," Human Genetics, vol. 130, No. 5, pp. 635-643 (2011).
De La Garza et al., "Evaluation of the dopamine B-hydroxylase (DBH) inhibitor nepicastat in participants who meet criteria for cocaine use disorder," Prog. Neuropsychopharmacol. Biol. Psychiatry, vol. 59, pp. 40-48 (2015).
Ella et al., "Association between dopamine beta hydroxylase rs5320 polymorphism and smoking behaviour in elderly Japanese," Journal of Human Genetics, vol. 57, No. 6, pp. 385-390 (2012).
Eriksson, E., "Amperozide, a putative anti-psychotic drug: uptake inhibition and release of dopamine in vitro in the rat brain," Life Sciences, vol. 47, No. 23, pp. 2111-2117 (1990).
Grenhoff et al., "Effects of amperozide, a putative antipsychotic drug, on rat midbrain dopamine neurons recorded in vivo," Pharmacology and Toxicology, Suppl 1, pp. 29-33 (1990).
Harvey et al., "Role of the serotonin 5-HT(2A) receptor in learning," Learning & Memory, vol. 10, No. 5, pp. 355-362 (2003).

(Continued)

*Primary Examiner* — Theodore R. Howell
*Assistant Examiner* — George W Kosturko
(74) *Attorney, Agent, or Firm* — Ice Miller LLP (57) ABSTRACT

Anti-cancer therapies involving non-cytotoxic dopamine beta-hydroxylase (DBH) inhibitors, such as nepicastat, etamicastat, and their analogs and pharmaceutically acceptable salts, and non-cytotoxic serotonin receptor antagonists, such as amperozide and its analogs and pharmaceutically acceptable salts are provided. The non-cytotoxic DBH inhibitors and serotonin receptor antagonists can be administered alone or in combination with one or more additional anti-cancer agents or anti-cancer therapies. Pharmaceutical compositions and combinations containing the non-cytotoxic DBH inhibitors and serotonin receptor antagonists and one or more additional anti-cancer agents, and methods of treating cancer using the pharmaceutical compositions and combinations are also provided.

4 Claims, 4 Drawing Sheets

(56) References Cited

OTHER PUBLICATIONS

Hegde et al., "Dopamine-beta-hydroxylase inhibition: a novel sympathomodulatory approach for the treatment of congestive heart failure," Current Pharmaceutical Design, vol. 4, No. 6, pp. 469-479 (1998).
Huang et al., "A phase I study to repurpose disulfiram in combination with temozolomide to treat newly diagnosed glioblastoma after chemoradiotherapy," J. Neurooncol., vol. 128, No. 2, pp. 259-266 (2016).
International Search Report and Written Opinion dated Oct. 10, 2017 in International Application No. PCT/US2017/044068.
Kontoghiorghes et al., "Cytotoxic and DNA-inhibitory effects of iron chelators on human leukaemic cell lines," Hematol. Oncol., vol. 4, No. 3, pp. 195-204 (1986).
Meltzer et al., "Effect of amperozide on rat cortical 5-HT2 and striatal and limbic dopamine D2 receptor occupancy implications for antipsychotic action," European Journal of Pharmacology, vol. 216, No. 1, pp. 67-71 (1992).
Mutschler et al., "Functional Polymorphism of the Dopamine B-Hydroxylase Gene is Associated With Increased Risk of Disulfiram-Induced Adverse Effects in Alcohol-Dependent Patients," Journal of Clinical Psychopharmacology, vol. 32, No. 4, pp. 578-580 (2012).
Nau, Jr., et al., "Serotonin 5-HT2A receptor activation blocks TNF-a mediated inflammation in vivo," PloS One, vol. 8, No. 10; e75426, pp. 1-8 (2013).
Nechushtan et al., A phase IIb trial assessing the addition of disulfiram to chemotherapy for the treatment of metastatic non-small cell lung cancer, Oncologist, vol. 20, No. 4, pp. 366-367 (2015).
Nunes et al., "Safety, tolerability, and pharmacokinetics of etamicastat, a novel dopamine-beta-hydroxylase inhibitor, in a rising multiple-dose study in young healthy subjects," Drugs in R & D, vol. 10, No. 4, pp. 225-242 (2010).
Ononye et al., "Tropolones as lead-like natural products: the development of potent and selective histone deacetylase inhibitors," ACS Med. Chem. Lett., vol. 4, No. 8, pp. 757-761 (2013).
Schweizer et al., "Pharmacodynamic study of disulfiram in men with non-metastatic recurrent prostate cancer," Prostate Cancer Prostatic Dis., vol. 16, No. 4, pp. 357-361 (2013).
Stanley et al., "Catecholamine modulatory effects of nepicastat (RS-25560-197), a novel, potent and selective inhibitor of dopamine-beta-hydroxylase," British Journal of Pharmacology, vol. 121, No. 8, pp. 1803-1809 (1997).
Svartengren et al., "Receptor binding properties of amperozide," Pharmacology and Toxicology, Suppl., vol. 1, pp. 8-11 (1990).
Van De Kar et al., "5-HT2A receptors stimulate ACTH, corticosterone, oxytocin, renin, and prolactin release and activate hypothalamic CRF and oxytocin-expressing cells," The Journal of Neuroscience 2001, vol. 21, No. 10, pp. 3572-3579 (2001).
Verma et al., A randomized phase II study of cisplatin alone versus cisplatin plus disulfiram, Am. J. Clin. Oncol., vol. 13, No. 2, pp. 119-124 (1990).
Williams et al., "The physiological role of 5-HT2A receptors in working memory," The Journal of Neuroscience, vol. 22, No. 7, pp. 2843-2854 (2002).
Yamamoto et al., "The effect of the atypical antipsychotic drug, amperozide, on carrier-mediated striatal dopamine release measured in vivo," Journal of Pharmacology and Experimental Therapeutics, vol. 263, No. 1, pp. 180-185 (1992).
Yu et al., "Serotonin 5-hydroxytryptamine(2A) receptor activation suppresses tumor necrosis factor-alpha-induced inflammation with extraordinary potency," The Journal of Pharmacology and Experimental Therapeutics, vol. 327, No. 2, pp. 316-323 (2008).
Zhang et al., "Evidence that 5-HT2A receptors in the hypothalamic paraventricular nucleus mediate neuroendocrine responses to (-)DOI," The Journal of Neuroscience, vol. 22, No. 21, pp. 9635-9642 (2002).
Ataee, R. et al., "The serotonin 5-HT2A receptor antagonist ritanserin induces apoptosis in human colorectal cancer and acts in synergy with curcumin," DN 160:42607, pp. 105-110, CAPLUS on STN, European Congress of Pharmacology, 6th, Granada, Spain, Jul. 17-20, 2013, Meeting Date 2012.
Sreevidya, C. et al., "Inhibition of Photocarcinogenesis by Platelet-Activating Factor or Serotonin Receptor Antagonists," Cancer Research, vol. 68, No. 10, pp. 3978-3984 (2008).
Daniel F. Manvich et al., "Dopamine [beta]-Hydroxylase Inhibitors Enhance the Discriminative Stimulus Effects of Cocaine in Rats", Journal of Pharmacology and Experimental Therapeutics, US, (Sep. 25, 2013), vol. 347, No. 3, doi: 10.1124/jpet.113.207746, ISSN 0022-3565, pp. 564-573, XP055669376.
Ana I. Loureiro et al., "Etamicastat, a new dopamine-β-hydroxylase inhibitor, pharmacodynamics and metabolism in rat", European Journal of Pharmacology, NL, (Oct. 1, 2014), vol. 740, doi:10.1016/j.ejphar.2014.07.027, ISSN 0014-2999, pp. 285-294, XP055669366.
Fernandez-Pol, et al., "Cytotoxic activity of fusaric acid on human adenocarcinoma cells in tissue culture," Anticancer Research, 1993, 13(1):57-64, Abstract Only.
Dhani, et al., "Fusaric Acid immunotoxicity and MAPK activation in normal peripheral blood mononuclear cells and Thp-1 cells," Scientific Reports, 7:3051, pp. 1-10.

* cited by examiner

USES OF DOPAMINE BETA-HYDROXYLASE (DBH) INHIBITORS AND SEROTONIN RECEPTOR (5-HT) ANTAGONISTS FOR THE TREATMENT OF CANCER

CROSS-REFERENCE TO RELATED APPLICATION

This application is a Section 371 of International Application No. PCT/US2017/044068, filed Jul. 27, 2017, which was published in the English language on Feb. 1, 2018 under International Publication No. WO 2018/022823 A1, which claims priority under 35 U.S.C. § 119(e) to U.S. Provisional Patent Application No. 62/367,728, filed Jul. 28, 2016, the disclosures of which are herein incorporated by reference in their entireties.

FIELD OF THE INVENTION

The invention relates to the use of dopamine beta-hydroxylase (DBH) inhibitors and serotonin receptor 2A (5-$HT_{2A}$) antagonists for the treatment of cancer.

BACKGROUND OF THE INVENTION

Dopamine Beta-Hydroxylase (DBH)

Dopamine beta-hydroxylase (DBH), also known as dopamine beta-monooxygenase, is an enzyme (EC 1.14.17.1) that in humans is encoded by the DBH gene. Dopamine beta-hydroxylase catalyzes the chemical reaction by which dopamine is oxidized by oxygen to norepinephrine, as shown in Scheme 1: Scheme 1: Oxidation of dopamine to norepinephrine catalyzed by DBH DBH is a 290 kDa copper-containing oxygenase consisting of four identical subunits, and its activity requires ascorbate as a cofactor [1].

DBH is the only enzyme involved in the synthesis of small-molecule membrane-bound neurotransmitters, making norepinephrine the only transmitter synthesized inside vesicles. Norepinephrine is expressed in noradrenergic nerve terminals of the central and peripheral nervous systems, as well as in chromaffin cells of the adrenal medulla.

DBH primarily contributes to the biosynthesis of trace amines and catecholamines, including epinephrine (adrenaline), norepinephrine (noradrenaline), and dopamine. It also participates in the metabolism of xenobiotics related to these substances. For example, the human DBH enzyme catalyzes beta-hydroxylation of amphetamine and para-hydroxy-amphetamine, producing norephedrine and para-hydroxynorephedrine, respectively [2-4].

DBH has been implicated as a correlating factor in conditions associated with decision making and addictive drugs, e.g., alcoholism [5] and smoking [6], attention deficit hyperactivity disorder [7], schizophrenia [8], and Alzheimer's disease [9]. Inadequate DBH is called dopamine beta hydroxylase deficiency.

DBH is inhibited by disulfiram [10], tropolone [11], and, most selectively, by nepicastat [12] and etamicastat [13]. Disulfiram is a drug that was discovered in the 1920s and is used to support the treatment of chronic alcoholism by inhibiting the enzyme acetaldehyde dehydrogenase and producing an acute sensitivity to ethanol (alcohol), meaning many of the effects of a "hangover" are felt immediately after alcohol is consumed. As a DBH inhibitor, disulfiram is also being studied as a treatment for cocaine dependence, as it prevents the breakdown of dopamine, a neurotransmitter whose release is stimulated by cocaine. The excess dopamine results in increased anxiety, higher blood pressure, restlessness, and other unpleasant symptoms. Disulfiram is also a proteasome inhibitor [14] that functions by creating complexes with metals (e.g., dithiocarbamate complexes), and represents a new approach to proteasome inhibition [15].

Despite promising preclinical results with disulfiram in inhibiting cancer growth, several clinical studies showed mixed results, and suggested that disulfiram has limited use in treating cancer patients. For example, in one phase I study where disulfiram was dosed alone in men with non-metastatic recurrent prostate cancer [16], the investigators concluded that further development of disulfiram should not be pursued in this population due to toxicity and lack of any clinical benefit. In another phase I study to treat newly diagnosed glioblastoma after chemoradiotherapy with a combination of disulfiram and temozolomide [17], the median progression-free survival (PFS) with 500 mg of disulfiram was 5.4 months, which is shorter as compared to 8.1 months from the previous chemoradiotherapy. The lack of significant improvement of PFS may be explained by the limited proteasome inhibition in patients, which is believed to be the mechanism of action of disulfiram.

The addition of disulfiram to chemotherapy such as cisplatin and vinorelbine appeared to prolong survival in patients with newly diagnosed non-small cell lung cancer in a phase II trial of 40 patients [18]. However, in another phase II study of 53 patients comparing the effects of disulfiram plus cisplatin to the effects of cisplatin alone [19], there was no statistically significant difference in response rate, time to progression, or median survival between the two groups. Contrary to previously published reports, disulfiram does not afford significant nephroprotection against cisplatin and, in fact, enhances gastrointestinal toxicity and ototoxicity. There are other cytotoxic DBH inhibitors, such as tropolone [20] with anti-cancer activities reported, but their mechanism of action in directly inhibiting cancer growth seems to be unrelated to their action on DBH. For example, tropolone and its derivatives displayed remarkable levels of selectivity for histone deacetylase 2 (HDAC2) and potently inhibited the growth of T-cell lymphocyte cell lines [21].

Serotonin Receptor 2A (5-$HT_{2A}$ Receptor)

The mammalian 5-$HT_{2A}$ receptor is a subtype of the three 5-HT2 receptors, A, B and C, that belongs to the serotonin receptor family and is a G protein-coupled receptor (GPCR) [22]. This is the main excitatory receptor subtype among the GPCRs for serotonin (5-HT), although 5-$HT_{2A}$ may also have an inhibitory effect [23] on certain areas, such as the visual cortex and the orbitofrontal cortex [24]. This receptor was first noted for its importance as a target of serotonergic psychedelic drugs, such as Lysergic acid diethylamide (LSD). Later, it came back to prominence because it was also found to mediate, at least partly, the action of many antipsychotic drugs, especially the atypical ones.

5-$HT_{2A}$ is expressed widely throughout the central nervous system (CNS). It is expressed near most of the serotoninergic terminal rich areas, including the neocortex (mainly prefrontal, parietal, and somatosensory cortex) and the olfactory tubercle. Especially high concentrations of this receptor on the apical dendrites of pyramidal cells in layer V of the cortex may modulate cognitive processes, working memory, and attention [24-26] by enhancing glutamate release followed by a complex range of interactions with the 5-$HT_{1A}$ [27], GABAA [28], adenosine A1 [29], AMPA [30], mGluR2/3 [31], mGlu5 [32], and OX2 receptors [33, 34]. In the periphery, it is highly expressed in platelets and many cell types of the cardiovascular system, in fibroblasts, and in neurons of the peripheral nervous system. Additionally, 5-HT2A mRNA expression has been observed in human monocytes [35].

The 5-$HT_{2A}$ receptor is known primarily to couple to the Gαq signal transduction pathway. Upon receptor stimulation with agonist, Gαq and β-γ subunits dissociate to initiate downstream effector pathways. Gαq stimulates phospholipase C (PLC) activity, which subsequently promotes the release of diacylglycerol (DAG) and inositol triphosphate (IP3), which in turn stimulate protein kinase C (PKC) activity and $Ca^{2+}$ release [36]. There are many additional signal cascade components that include the formation of arachidonic acid through PLA2 activity, activation of phospholipase D, Rho/Rho kinase, and ERK pathway activation initiated by agonist stimulation of the receptor.

Physiological processes mediated by the 5-$HT_{2A}$ receptor include:

CNS: neuronal excitation, behavioral effects, learning, anxiety;

Smooth muscle: contraction (in gastrointestinal tract & bronchi);

Vasoconstriction/vasodilation;

Platelets: aggregation

Memory [26, 37, 38]

Activation of the 5-$HT_{2A}$ receptor with 1-(2,5-dimethoxy-4-iodophenyl)-2-aminopropane (DOI) produces potent anti-inflammatory effects in several tissues including cardiovascular and gut tissues. Other 5-$HT_{2A}$ agonists, such as LSD, also have potent anti-inflammatory effects against TNF-α-induced inflammation [39, 40]. Activation of the 5-$HT_{2A}$ receptor in the hypothalamus causes increases in hormonal levels of oxytocin, prolactin, ACTH, corticosterone, and renin [41, 42].

Nepicastat and etamicastat are highly selective DBH inhibitors. Nepicastat, also known as SYN117 and RS-25560-197, has been studied as a possible treatment for congestive heart failure, and appears to be well tolerated as such [43]. Nepicastat and its analogs, such as etamicastat, share a common potential use in treating hypertension. Clinical trials to assess nepicastat as a treatment for post-traumatic stress disorder (PTSD) and cocaine dependence have also been completed. Nepicastat is safe when co-administered with cocaine and may suppress its positive subjective effects, suggesting it as a pharmacotherapy for treatment of cocaine use disorder [44]. With a lower level of brain-blood-barrier penetration, etamicastat (BIA 5-453) is a dopamine-β-hydroxylase inhibitor that decreases norepinephrine levels in peripheral sympathetically innervated tissues, without having effects in brain tissues of spontaneously hypertensive rats [45]. In a phase II clinical study, etamicastat was observed to dose-dependently decrease systolic and diastolic blood pressure after 10 days of treatment [46].

Amperozide is an atypical antipsychotic of the diphenyl-butyl-piperazine class which acts as an antagonist at the 5-$HT_{2A}$ receptor [47]. It does not block dopamine receptors as with most antipsychotic drugs [48], but does inhibit dopamine release [49, 50] and alter the firing pattern of dopaminergic neurons [51]. It was investigated for the treatment of schizophrenia in humans [52] but never adopted clinically. Its main use is instead in veterinary medicine, primarily in intensively farmed pigs, for decreasing aggression and stress and thereby increasing feeding and productivity [53-56].

To the best of the knowledge of the inventors, anti-cancer activities of nepicastat, emicastat, and amperozide, either in vitro or in vivo, have not been reported.

BRIEF SUMMARY OF THE INVENTION

There is a need in the art for improved methods of treating cancer that achieve effective treatment yet have reduced cytotoxic or other side effects. The invention is based on the surprising finding that non-cytotoxic serotonin receptor (5-HT) antagonists and non-cytotoxic dopamine β-hydroxylase (DBH) inhibitors, particularly nepicastat, emicastat, and amperozide and their analogs and pharmaceutically acceptable salts have anti-cancer activity and can be used to treat cancer, alone or in combination with one or more additional anti-cancer therapies and/or anti-cancer agents, such as a chemotherapeutic agent, targeted therapy agent, or an immunotherapy agent.

In one general aspect, the invention relates to a method of treating cancer in a subject in need thereof, the method comprising administering to the subject a pharmaceutical composition comprising a therapeutically effective amount of a non-cytotoxic serotonin receptor (5-HT) antagonist or a non-cytotoxic dopamine β-hydroxylase (DBH) inhibitor, and a pharmaceutically acceptable carrier.

In one embodiment, the method comprises administering to the subject a pharmaceutical composition comprising a therapeutically effective amount of a non-cytotoxic serotonin receptor (5-HT) antagonist, particularly a serotonin receptor 2A (5-$HT_{2A}$) antagonist, such as amperozide or an analog thereof, or a pharmaceutically acceptable salt thereof, and a pharmaceutically acceptable carrier.

In another embodiment, the method comprises administering to the subject a pharmaceutical composition comprising a therapeutically effective amount of a non-cytotoxic DBH inhibitor, such as nepicastat or etamicastat, or an analog thereof or a pharmaceutically acceptable salt thereof, and a pharmaceutically acceptable carrier.

In certain embodiments of the invention, the pharmaceutical composition comprising the non-cytotoxic 5-HT antagonist or non-cytotoxic DBH inhibitor is administered in combination with at least one additional anti-cancer agent, for instance a chemotherapeutic agent, a targeted therapy agent, and an immunotherapy agent.

In some embodiments of the invention, the cancer to be treated is colon cancer, breast cancer, liver cancer, melanoma, lung cancer, prostate cancer, ovarian cancer, pancreatic cancer, cervical cancer, renal cell carcinoma, bladder cancer, or gastric cancer.

In another general aspect, the invention relates to a pharmaceutical combination comprising:

(a) a first pharmaceutical composition comprising a therapeutically effective amount of a compound selected from the group consisting of amperozide, nepicastat, and etamicastat, or an analog thereof, or a pharmaceutically acceptable salt thereof, and a pharmaceutically acceptable carrier; and (b) a therapeutically effective amount of at least one additional anti-cancer agent selected from the group consisting of a chemotherapeutic agent, a targeted therapy agent, and an immunotherapy agent, wherein the therapeutically effective amount of the at least one additional anti-cancer agent is present in the first composition or in a second composition to be administered in combination with the first composition.

Other aspects of the invention relate to methods of manufacturing pharmaceutical compositions and combinations of the invention, and methods of treating cancer with the pharmaceutical compositions and combinations of the invention.

Other aspects, features and advantages of the invention will be apparent from the following disclosure, including the detailed description of the invention and its preferred embodiments and the appended claims.

BRIEF DESCRIPTION OF THE FIGURES

FIGS. 2A and 2B show the effects of amperozide treatment as compared to paclitaxel treatment on in vivo tumor growth in an H22 murine hepatic cancer xenograft model as described in Example 4.

FIGS. 3A and 3B show the effects of nepicastat treatment as compared to paclitaxel treatment on in vivo tumor growth in an H22 murine hepatic cancer xenograft model as described in Example 4.

FIGS. 4A and 4B show the effects of nepicastat and etamicastat treatment compared to anti-PD-1 mAb treatment (intraperitoneal administration) on in vivo tumor growth in an H22 hepatic cancer xenograft model as described in Example 5; FIGS. 5A and 5B show the effects of nepicastat treatment on in vivo tumor growth and body weight in CT-26 murine colon cancer and EMT-6 murine breast cancer xenograft models as described in Example 6.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the cancer. In a particular embodiment, "treat," "treating," and "treatment" refer to an alleviation, prevention of the development or onset, or reduction in the duration of one or more symptoms associated with the cancer. In a particular embodiment, "treat," "treating," and "treatment" refer to prevention of the recurrence of the cancer. In a particular embodiment, "treat," "treating," and "treatment" refer to an increase in the survival of a subject having the cancer. In a particular embodiment, "treat," "treating," and "treatment" refer to elimination of the cancer in the subject.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

As used herein, the term "effective amount" or "therapeutically effective amount" refers to an amount of an active ingredient or component that elicits the desired biological or medicinal response in a subject. In particular embodiments, the effective amount is the amount of an active ingredient or compound that is effective to achieve a synergistic effect with another active ingredient or compound. A therapeutically effective amount can be determined empirically and in a routine manner, in relation to the stated purpose. For example, in vitro assays can optionally be employed to help identify optimal dosage ranges. Selection of a particular effective dose can be determined (e.g., via clinical trials) by those skilled in the art based upon the consideration of several factors, including the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems.

The phrase "pharmaceutically acceptable salt" as used herein means those salts of a compound of interest that are safe and effective for pharmaceutical use in mammals and that possess the desired biological activity. Pharmaceutically acceptable salts include base addition salts, which are salts of basic groups present in the specified compounds, and acid addition salts, which are salts of acid groups present in the specific compounds. The acidic or basic groups can be organic or inorganic. For a review on pharmaceutically acceptable salts see Berge et al., 66 *J. Pharm. Sci.* 1-19 (1977), which is incorporated herein by reference.

As used herein, the phrases "anti-cancer agent," "anti-cancer drug," and "anti-cancer therapy" refer to any substance or treatment that can be used to cause regression, prevent or slow the progression, eliminate or prevent the recurrence of a cancer, or increase the survival rate of a subject having the cancer. Typically, the terms "agent" and "drug" are used with reference to a substance (e.g., small molecule compound, antibody, etc.) whereas the term "therapy" is used with reference to a treatment method. Anti-cancer agents can exert their effects by a variety of mechanisms including, but not limited to, stimulation of an immune response, inhibition of immune-suppression, and/or inhibition of cell proliferation. Examples of anti-cancer agents or drugs include, but are not limited to, chemotherapeutic agents, immunotherapy agents, and targeted therapy agents. Examples of anti-cancer therapies include, but are not limited to surgery, gene therapy, radiotherapy, and cryotherapy.

As used herein, the terms "chemotherapeutic agent" and "targeted therapy agent" refer to any chemical substance that is an anti-cancer drug or anti-cancer agent. In general, chemotherapeutic and targeted therapy agents are substances that block the growth and proliferation of cancer cells. Chemotherapeutic agents are often cytotoxic, meaning that they kill tumor cells, but they can also kill normal healthy cells because they typically function throughout the body. Unlike chemotherapy agents, targeted therapy agents take advantage of the differences between normal cells and cancer cells, and block the growth or proliferation of cancer cells by interacting with molecules specific to the cancer cells that are usually involved in the growth, progression and spread of the cancer.

As used herein, the term "immunotherapy agent" or "immunotherapy modulator" refers to any agent that is capable of stimulating an immune response and/or inhibiting immune-suppression. Cancer immunotherapy attempts to stimulate the immune system to reject and destroy tumors.

As used herein, the phrases "in combination" and "in combination with" in the context of the administration of two or more therapies to a subject, refers to the use of more than one therapy. The use of the phrases "in combination" and "in combination with" does not restrict the order in which the therapies are administered to a subject. For example, a first therapy (e.g., an effective amount of a DBH inhibitor or serotonin receptor 2A antagonist) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., an effective amount of an immunotherapy agent, a chemotherapeutic agent, or a targeted therapy agent) to a subject.

Methods and Compositions

The invention relates to methods of treating cancers and tumors with non-cytotoxic DBH inhibitors, such as nepicastat, etamicastat, and analogs thereof, and non-cytotoxic 5-HT antagonists, particularly 5-HT$_{2A}$ antagonists, such as amperozide and analogs thereof, alone or in combination with one or more anti-cancer agents and/or anti-cancer therapies.

As used herein, a "DBH inhibitor" is any compound that inhibits the enzyme dopamine β-hydroxylase (DBH). DBH catalyzes the oxidation of dopamine to norepinephrine. DBH inhibitors include compounds that reduce or prevent the oxidation of dopamine to norepinephrine catalyzed by DBH. In particular, "a non-cytotoxic DBH inhibitor" is any compound that inhibits the enzyme DBH and inhibits or reduces tumor growth in vivo, but has reduced cytotoxic effects (e.g., killing of cancer cells) in vitro. Examples of DBH inhibitors include, but are not limited to, nepicastat, etamicastat, disulfiram, and tropolone. Etamicastat is also considered an analog of nepicastat. Examples of non-cytotoxic DBH inhibitors include, but are not limited to, nepicastat and etamicastat, and pharmaceutically acceptable salts thereof. In preferred embodiments of the invention, the DBH inhibitor is selected from nepicastat and etamicastat, or a pharmaceutically acceptable salt thereof.

As used herein, a "5-HT antagonist" is any compound that dampens or blocks a biological response mediated by the 5-HT receptor. In particular, "5-HT$_{2A}$ antagonist" is any compound that dampens or blocks a biological response mediated by the 5-HT$_{2A}$ receptor. The 5-HT$_{2A}$ receptor is a G protein-coupled receptor (GPCR) that is part of the serotonin receptor family. As used herein, "a non-cytotoxic 5-HT antagonist" is any compound that inhibits or reduces tumor growth in vivo by dampening or blocking a biological response mediated by the 5-HT receptor, but has reduced cytotoxic effects (e.g., killing of cancer cells) in vitro. Examples of 5-HT antagonists, particularly 5-HT$_{2A}$ antagonists include, but are not limited to amperozide.

As used herein, "nepicastat," "etamicastat," and "amperozide" refer to compounds having the following chemical structures:

Nepicastat

-continued

Etamicastal amperozide

In one embodiment of the invention, a method of treating cancer in a subject in need thereof comprises administering to the subject a pharmaceutical composition comprising a therapeutically effective amount of amperozide or an analog thereof, or a pharmaceutically acceptable salt thereof, and a pharmaceutically acceptable carrier.

In another embodiment of the invention, a method of treating cancer in a subject in need thereof comprises administering to the subject a pharmaceutical composition comprising a therapeutically effective amount of nepicastat or an analog thereof, or a pharmaceutically acceptable salt thereof and a pharmaceutically acceptable carrier.

In yet another embodiment of the invention, a method of treating cancer in a subject in need thereof comprises administering to the subject a pharmaceutical composition comprising a therapeutically effective amount of etamicastat, or an analog thereof, or a pharmaceutically acceptable salt thereof, and a pharmaceutically acceptable carrier.

Cancer is an unregulated proliferation of cells due to loss of normal controls, resulting in abnormal growth, lack of differentiation, local tissue invasion, and often, metastasis. Tumor is an abnormal growth of cells or tissues which may be benign or malignant. Any cancer or tumor can be treated according to the methods of the invention as described herein, including, but not limited to, colon cancer, breast cancer, liver cancer, melanoma, lung cancer, prostate cancer, ovarian cancer, pancreatic cancer, cervical cancer, renal cell carcinoma, bladder cancer, or gastric cancer.

In some embodiments, the cancer is colon cancer, breast cancer, liver cancer, or melanoma. In other embodiments, the cancer is a chemotherapy-resistant, immunotherapy-resistant or radio-resistant cancer, such as a chemotherapy-resistant, immunotherapy-resistant or radio-resistant breast cancer, liver cancer, colon cancer, or melanoma.

The compounds, agents, or pharmaceutical compositions described herein can be administered by any acceptable route. For example, the compounds, agents, or pharmaceutical compositions described herein can be administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in creams, in lipid compositions, via a catheter, via a lavage, via continuous infusion, via infusion, via inhalation, via injection, via local delivery, via localized perfusion, by bathing target cells directly, or any combination thereof.

Pharmaceutical compositions according to the invention can be formulated for any form of administration including injectable (intravenous), mucosa, oral (solid and liquid preparations), inhalation, ocular, rectal, topical, or parenteral (infusion, injection, implantation, subcutaneous, intravenous, intraarterial, intramuscular) administration. Examples of solid preparations for oral administration include, but are not limited to, powders, capsules, caplets, gelcaps, and tablets; examples of liquid preparations for oral or mucosal administration include, but are not limited to, suspensions, emulsions, elixirs, and solutions; and examples of topical formulations include, but are not limited to, emulsions, gels, ointments, creams, patches, pastes, foams, lotions, drops, or serums. Examples of preparations for parenteral administration include, but are not limited to injectable solutions, dry products that can be dissolved or suspended in a pharmaceutically acceptable carrier for injection, injectable suspensions, and injectable emulsions. Examples of other suitable compositions include eye drops and other opthalmalic preparations; aerosols, such as nasal sprays or inhalers; liquid dosage forms suitable for parenteral administration; suppositories; and lozenges.

In preferred embodiments, pharmaceutical compositions comprising the DBH inhibitors and/or 5-HT antagonists are formulated for oral administration, including solid preparations, such as powders, capsules, caplets, gelcaps, and tablets; and liquid preparations, such as suspensions, emulsions, elixirs, and solutions.

Pharmaceutical compositions according to the invention further comprise a pharmaceutically acceptable carrier, such as those widely-employed in the art of drug manufacturing. As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. Pharmaceutically acceptable carriers in particular are non-toxic, and can include one or more of binding agents, such as hydroxypropylmethylcellulose; solubilizing agents, such as povidone and cetylpyridinium chloride; acidifying agents, such as alginic acid; pore forming agents, such as sucrose; lubricants, such as stearyl fumarate; glidants, such as colloidal silicon dioxide; binders, suspending agents, emulsifying agents, diluents, fillers, granulating agents adhesives, disintegrants, antiadherants, wetting agents, gelling agents, buffers, chelating agents, preservatives, colorants, flavorants, and sweeteners and the like. Pharmaceutically acceptable carriers can take a wide variety of forms dependent on the form of preparation desired for administration, and the amount and type will vary according to the need. One of ordinary skill in the art will readily be able to determine the appropriate carriers to be added to a pharmaceutical composition of the invention in view of the present disclosure. Non-limiting examples of carriers include saline and water.

The dosage of DBH inhibitors and/or 5-HT antagonists is selected, e.g., based on required dose, fluid volumes, viscosities, etc., according to the particular mode of administration selected. In some embodiments, a DBH inhibitor or 5-HT antagonist is administered, preferably orally administered, in a dosage of about 1 mg/day to 4 g/day, such as 1 mg/day, 10 mg/day, 50 mg/day, 100 mg/day, 200 mg/day, 300 mg/day, 400 mg/day, 500 mg/day, 600 mg/day, 700 mg/day, 800 mg/day, 900 mg/day, 1 g/day, 2 g/day, 3 g/day, or 4 g/day. For example, nepicastat or a pharmaceutically acceptable salt thereof can be administered, e.g., to a human subject, in a dosage of about 20 mg/day to 2.5 g/day, preferably 40 mg/day to 1.0 g/day, and more preferably 80 mg/day to 500 mg/day); amperozide or a pharmaceutically acceptable salt thereof can be administered, e.g., to a human subject, in a dosage of about 1 mg/day to 100 mg/day, preferably 2 mg/day to 50 mg/day, and more preferably 4 mg/day to 25 mg/day; and etamicastat can be administered, e.g., to a human subject, in a dosage of about 40 mg/day to 4.0 g/day, preferably 80 mg/day to 2.0 g/day, and more preferably 160 mg/day to 1.0 g/day.

In some embodiments, the DBH inhibitors and/or 5-HT antagonists or compositions thereof are administered once daily. In other embodiments, the DBH inhibitors and/or 5-HT antagonists or compositions thereof are administered twice daily. In other embodiments, the DBH inhibitors and/or 5-HT antagonists or compositions thereof are administered multiple times a day, once every two days, once every three days, once every four days, once every five days, once every six days, once every seven days, once every two weeks, once every three weeks, once every four weeks, once every two months, once every three months, once every four months, once every five months, once every six months, or once per year. The DBH inhibitors and/or 5-HT antagonists or compositions thereof can be administered for one day, two days, three days, four days, five days, six days, seven days, two weeks, three weeks, four weeks, two months, three months, four months, five months, six months, one year, two years three years, four years, five years, ten years, or fifteen years, etc.

According to embodiments of the invention, the DBH inhibitors and/or 5-HT antagonists can be used alone or in combination with additional anti-cancer therapies and/or anti-cancer agents. In some embodiments, the additional anti-cancer therapy or anti-cancer agent comprises surgery, radiotherapy, chemotherapy or a chemotherapeutic agent, toxin therapy, immunotherapy or an immunotherapy agent, a targeted therapy agent, cryotherapy or gene therapy. When an anti-cancer agent is used, the DBH inhibitor and/or 5-HT antagonist can be administered together in the same composition as the additional anti-cancer agent. Alternatively, the DBH inhibitor and/or 5-HT antagonist and the additional anti-cancer agent can be administered in separate compositions. When administered as separate compositions, the DBH inhibitor and/or 5-HT antagonist can be administered by the same form of administration (e.g., both via oral administration) or by a different route of administration than that used for the additional anti-cancer agent (e.g., oral administration for the DBH inhibitor and/or 5-HT antagonist and injection for the additional anti-cancer agent).

Other aspects of the invention relate to pharmaceutical compositions and combinations comprising DBH inhibitors and/or 5-HT antagonists; at least one additional anti-cancer agent; and a pharmaceutically acceptable carrier. Any DBH inhibitor and/or 5-HT antagonist can be used in the compositions of the invention in view of the present disclosure, including but not limited to, amperozide, nepicastat, etamicastat, analogs thereof, and pharmaceutically acceptable salts thereof.

Pharmaceutical compositions can be prepared by any method known in the art in view of the present disclosure, and one of ordinary skill in the art will be familiar with such techniques used to prepare pharmaceutical compositions. For example, a pharmaceutical composition of the invention can be prepared by combining the DBH inhibitor (e.g., nepicastat, etamicastat, etc.) or 5-HT antagonist (e.g., amperozide, etc.), at least one additional anti-cancer agent, and a pharmaceutically acceptable carrier.

Embodiments of the invention also relate to methods of treating cancer with the pharmaceutical compositions and combinations described herein. According to embodiments of the invention, the method comprises administering the pharmaceutical composition or combination to a subject in need thereof. The method can be used to treat any cancer in view of the present disclosure, and can be administered to a subject in need of the treatment by any suitable route in view of the present disclosure.

EMBODIMENTS

Embodiment 1 is a method of treating a cancer or tumor in a subject in need thereof, the method comprising administering to the subject a pharmaceutical composition comprising a therapeutically effective amount of a non-cytotoxic serotonin receptor (5-HT) antagonist or a pharmaceutically acceptable salt thereof, and a pharmaceutically acceptable carrier.

Embodiment 2 is a method of treating a cancer or tumor in a subject in need thereof, the method comprising administering to the subject a pharmaceutical composition comprising a therapeutically effective amount of a non-cytotoxic dopamine β-hydroxylase (DBH) inhibitor or a pharmaceutically acceptable salt thereof, and a pharmaceutically acceptable carrier.

Embodiment 3 is the method of embodiment 1, wherein the non-cytotoxic 5-HT antagonist is amperozide or an analog thereof, or a pharmaceutically acceptable salt thereof.

Embodiment 4 is the method of embodiment 2, wherein the non-cytotoxic DBH inhibitor is nepicastat or an analog thereof, or a pharmaceutically acceptable salt thereof.

Embodiment 5 is the method of embodiment 2, wherein the non-cytotoxic DBH inhibitor is etamicastat or an analog thereof, or a pharmaceutically acceptable salt thereof.

Embodiment 6 is the method of any one of embodiments 1-5, wherein the pharmaceutical composition is administered orally to the subject.

Embodiment 7 is the method of any one of embodiments 1-6, further comprising administering to the subject a therapeutically effective amount of at least one additional anti-cancer agent selected from the group consisting of a chemotherapeutic agent, a targeted therapy agent, and an immunotherapy agent.

Embodiment 8 is the method of embodiment 7, wherein the at least one additional anti-cancer agent is an immunotherapy agent.

Embodiment 9 is the method of any one of embodiments 1-8, wherein the treatment is performed in combination with at least one additional anti-cancer therapy selected from the group consisting of surgery, gene therapy, radiotherapy, and cryotherapy.

Embodiment 10 is the method of any one of embodiments 1-9, wherein the cancer is selected from the group consisting of colon cancer, breast cancer, liver cancer, melanoma, lung cancer, prostate cancer, ovarian cancer, pancreatic cancer, cervical cancer, renal cell carcinoma, bladder cancer, and gastric cancer.

Embodiment 11 is the method of embodiment 10, wherein the cancer is breast cancer, colon cancer, liver cancer, or melanoma.

Embodiment 12 is a pharmaceutical composition comprising a therapeutically effective amount of a non-cytotoxic dopamine β-hydroxylase (DBH) inhibitor or a pharmaceutically acceptable salt thereof, for instance nepicastat or etamicastat, or a pharmaceutically acceptable salt thereof; at least one additional anti-cancer agent selected from the group consisting of a chemotherapeutic agent, a targeted therapy agent, and an immunotherapy agent; and a pharmaceutically acceptable carrier.

Embodiment 13 is a pharmaceutical composition comprising a therapeutically effective amount of a non-cytotoxic serotonin receptor (5-HT) antagonist or a pharmaceutically acceptable salt thereof, for instance amperozide or a pharmaceutically acceptable salt thereof; at least one additional anti-cancer agent selected from the group consisting of a chemotherapeutic agent, a targeted therapy agent, and an immunotherapy agent; and a pharmaceutically acceptable carrier.

Embodiment 14 is a method of manufacturing the pharmaceutical composition of embodiment 12, the method comprising combining the non-cytotoxic DBH inhibitor or the pharmaceutically acceptable salt thereof; the at least one additional anti-cancer agent; and the pharmaceutically acceptable carrier.

Embodiment 15 is a method of manufacturing the pharmaceutical composition of embodiment 13, the method comprising combining the non-cytotoxic 5-HT antagonist, or the pharmaceutically acceptable salt thereof; the at least one additional anti-cancer agent; and the pharmaceutically acceptable carrier.

Embodiment 16 is a pharmaceutical combination comprising:
  (a) a first composition comprising a therapeutically effective amount of a compound selected from the group consisting of amperozide, nepicastat, and etamicastat or an analog thereof or a pharmaceutically acceptable salt thereof, and a pharmaceutically acceptable carrier; and
  (b) a therapeutically effective amount of at least one additional anti-cancer agent selected from the group consisting of a chemotherapeutic agent, a targeted therapy agent, and an immunotherapy agent,
wherein the therapeutically effective amount of the at least one additional anti-cancer agent is present in the first composition or in a second composition to be administered in combination with the first composition.

Embodiment 17 is the pharmaceutical combination of embodiment 16, wherein the first composition comprises a therapeutically effective amount of nepicastat or a pharmaceutically acceptable salt thereof.

Embodiment 18 is the pharmaceutical combination of embodiment 16, wherein the first composition comprises a therapeutically effective amount of etamicastat or a pharmaceutically acceptable salt thereof.

Embodiment 19 is the pharmaceutical combination of embodiment 16, wherein the first composition comprises a therapeutically effective amount of amperozide or a pharmaceutically acceptable salt thereof.

Embodiment 20 is a method of treating a cancer or tumor in a subject in need thereof, the method comprising administering to the subject the pharmaceutical composition of any one of embodiments 12-13 or the pharmaceutical combination of any one of embodiments 16-19.

Embodiment 21 is the method of embodiment 20, wherein the cancer or tumor is selected from the group consisting of colon cancer, breast cancer, liver cancer, melanoma, lung cancer, prostate cancer, ovarian cancer, pancreatic cancer, cervical cancer, renal cell carcinoma, bladder cancer, and gastric cancer.

Embodiment 22 is the method of embodiment 21, wherein the cancer is breast cancer, colon cancer, liver cancer, or melanoma.

Embodiment 23 is the method of any one of embodiments 1-11 and 20-22, wherein the subject is a human subject.

Embodiment 24 is the pharmaceutical composition of any one of embodiments 12-13 or the pharmaceutical combination of any one of embodiments 16-19 for use in treating a cancer in a subject in need thereof.

Embodiment 25 is a pharmaceutical composition for use in treating a cancer in a subject in need thereof, the pharmaceutical composition comprising a therapeutically effective amount of a non-cytotoxic serotonin receptor (5-HT) antagonist or a pharmaceutically acceptable salt thereof, and a pharmaceutically acceptable carrier.

Embodiment 26 is a pharmaceutical composition for use in treating a cancer in a subject in need thereof, the pharmaceutical composition comprising a therapeutically effective amount of a non-cytotoxic dopamine β-hydroxylase (DBH) inhibitor or a pharmaceutically acceptable salt thereof, and a pharmaceutically acceptable carrier.

Embodiment 27 is the pharmaceutical composition for use of embodiment 25, wherein the non-cytotoxic 5-HT antagonist is amperozide or an analog thereof, or a pharmaceutically acceptable salt thereof.

Embodiment 28 is the pharmaceutical composition for use of embodiment 26, wherein the non-cytotoxic DBH inhibitor is nepicastat or an analog thereof, or a pharmaceutically acceptable salt thereof.

Embodiment 29 is the pharmaceutical composition for use of embodiment 26, wherein the non-cytotoxic DBH inhibitor is etamicastat or an analog thereof, or a pharmaceutically acceptable salt thereof.

Embodiment 30 is the pharmaceutical composition for use of any one of embodiments 25-29, wherein the pharmaceutical composition is formulated for oral administration.

Embodiment 31 is the pharmaceutical composition for use of any one of embodiments 25-30, wherein the pharmaceutical composition is used in combination with a therapeutically effective amount of at least one additional anti-cancer agent selected from the group consisting of a chemotherapeutic agent, a targeted therapy agent, and an immunotherapy agent.

Embodiment 32 is the pharmaceutical composition for use of embodiment 31, wherein the at least one additional anti-cancer agent is an immunotherapy agent Embodiment 33 is the pharmaceutical composition for use of any one of embodiments 25-32, wherein the pharmaceutical composition is used in combination with at least one additional anti-cancer therapy selected from the group consisting of surgery, gene therapy, radiotherapy, and cryotherapy.

Embodiment 34 is the pharmaceutical composition for use of any one of embodiments 25-33, wherein the cancer is selected from the group consisting of colon cancer, breast cancer, liver cancer, melanoma, lung cancer, prostate cancer, ovarian cancer, pancreatic cancer, cervical cancer, renal cell carcinoma, bladder cancer, and gastric cancer.

Embodiment 35 is the pharmaceutical composition for use of embodiment 34, wherein the cancer is breast cancer, colon cancer, liver cancer, or melanoma.

Embodiment 36 is use of a non-cytotoxic serotonin receptor (5-HT) antagonist or a pharmaceutically acceptable salt thereof in the manufacture of a medicament for treating cancer.

Embodiment 37 is use of a non-cytotoxic dopamine β-hydroxylase (DBH) inhibitor or a pharmaceutically acceptable salt thereof in the manufacture of a medicament for treatment cancer.

Embodiment 38 is use of embodiment 36, wherein the non-cytotoxic 5-HT antagonist is amperozide or an analog thereof, or a pharmaceutically acceptable salt thereof.

Embodiment 39 is use of embodiment 37, wherein the non-cytotoxic DBH inhibitor is nepicastat or an analog thereof, or a pharmaceutically acceptable salt thereof.

Embodiment 40 is use of embodiment 37, wherein the non-cytotoxic DBH inhibitor is etamicastat or an analog thereof, or a pharmaceutically acceptable salt thereof.

Embodiment 41 is use of any one of embodiments 36-40, wherein the medicament is formulated for oral administration.

Embodiment 42 is use of the pharmaceutical composition of embodiment 12 or 13 in the manufacture of a medicament for treating cancer.

Embodiment 43 is use of the pharmaceutical combination of any one of embodiments 16-19 in the manufacture of a medicament for treating cancer.

Embodiment 44 is use of any one of embodiments 36 to 43, wherein the cancer is selected from the group consisting of colon cancer, breast cancer, liver cancer, melanoma, lung cancer, prostate cancer, ovarian cancer, pancreatic cancer, cervical cancer, renal cell carcinoma, bladder cancer, and gastric cancer.

Embodiment 45 is use of embodiment 44, wherein the cancer is breast cancer, colon cancer, liver cancer, or melanoma.

Embodiment 46 is the method of any one of embodiments 3, 6-11, and 20-22, wherein amperozide, or the analog thereof or pharmaceutically acceptable salt thereof is administered at a dose of about 1 mg/day to 100 mg/day, preferably 2 mg/day to 50 mg/day, and more preferably 4 mg/day to 25 mg/day.

Embodiment 47 is the method of any one of embodiments 4, 6-11, and 20-22, wherein nepicastat or the analog thereof or pharmaceutically acceptable salt thereof is administered at a dose of about 20 mg/day to 2.5 g/day, preferably 40 mg/day to 1.0 g/day, and more preferably 80 mg/day to 500 mg/day.

Embodiment 48 is the method of any one of embodiments 5-11 and 20-22, wherein etamicastat or the analog thereof or pharmaceutically acceptable salt thereof is administered at a dose of about 40 mg/day to 4.0 g/day, preferably 80 mg/day to 2.0 g/day, and more preferably 160 mg/day to 1.0 g/day.

The following examples of the invention are to further illustrate the nature of the invention. It should be understood that the following examples do not limit the invention and that the scope of the invention is to be determined by the appended claims.

EXAMPLES

Example 1: Experimental Procedure for the In Vitro Cell Proliferation Assay in H22 Murine Hepatocarcinoma Cell Line Materials and Methods:

Materials:

| Cell Line | Source | Culture Medium |
| --- | --- | --- |
| H22 | China Center for Type Culture Collection, CCTCC | RPMI-1640 medium + 10% FBS |

Reagents:

1. Compounds: amperozide, nepicastat
2. Positive control compound: Paclitaxel
3. CTG assay kit: (Promega)—Cat No. G7572
4. RPMI-1640 medium (Invitrogen)—Cat No. 11875093
5. PBS (Hyclone)—Cat No. SH30256-01B
6. Trypsin/EDTA (Invitrogen)—25200-056
7. FBS (Biowest)—Cat No. S1580-500
8. Penicillin-Streptomycin liquid (Invitrogen)—Cat No. 15140-122
9. 96-well white plate (Costar)—Cat No. 3917

Instruments: EnVision 2104 Multilabel Reader

Methods:

(1) Cells were cultured in RPMI-1640 medium supplemented with 10% FBS, 100 U/ml penicillin, and 100 mg/ml streptomycin at 37° C. and 5% $CO_2$ atmosphere. Cells that were 80% confluent were used in the assay.

(2) Cells were spun at 1000 rpm for 4 minutes, resuspended in fresh medium supplemented with 10% FBS, and then the cell density was adjusted and the cells were seeded in a 96-well white plate, 3000 cells/well/ 90 μl of H22 cells, 3 wells/group.

(3) After 24 hours, a 10× compound solution was prepared and 10 μl of the 10× compound solution was transferred to each well to get the final concentrations 1 μM and 0.1 μM (Solvent control: 0.1% DMSO; Blank control: without cells, for instrument auto zero).

(4) The cells were incubated with the compound for 72 hours at 37° C. and 5% $CO_2$ atmosphere.

(5) The plate and its contents were equilibrated at room temperature for 30 minutes.

(6) Then, 100 μL of the CellTiter-Glo®Reagent were added to each well in the 96-well white plate.

(7) The contents were mixed for 2 minutes on an orbital shaker to induce cell lysis.

(8) The plate was allowed to incubate at room temperature for 10 minutes to stabilize the luminescent signal.

(9) Luminescence was recorded using an EnVision 2104 Multilabel Reader.

Example 2: Experimental Procedures for Testing In Vivo Tumor Growth in Murine H22, CT-26 and EMT-6 Xenograft Models Experiments using the murine H22, CT-26 and EMT-6 xenograft models were performed as described below.

Cell Lines and Animals:

| Model | Cell line | Cells number for Inoculation | Mouse (*Mus Musculus*) Strain |
|---|---|---|---|
| H22 | H22 (CCTCC) | $1 \times 10^6/0.1$ mL | Balb/c (Shanghai Lingchang Bio-Technology) |
| CT-26 | CT-26 (ATCC) | $5 \times 10^5/0.1$ mL | Balb/c (Shanghai Lingchang Bio-Technology) |
| EMT-6 | EMT-6 (ATCC) | $5 \times 10^5/0.1$ mL | Balb/c (Shanghai Lingchang Bio-Technology) |

Testing Articles:

| Product identification | Supplier | Storage condition | Vehicle |
|---|---|---|---|
| Paclitaxel | Beijing SL Pharm | 4° C. and in dark | Saline |
| Amperozide | Aldrich | 4° C. and in dark | 0.5% MC |
| Nepicastat HCl | Tocris Bioscience | 4° C. and in dark | 0.5% MC |
| Etamicastat | Pharmaron | 4° C. and in dark | 0.5% MC |
| Anti-PD-1 (RMP1-14) | BioXcell | 4° C. and in dark | Saline |

Cell Culture:

Cells were cultured in RPMI-1640 medium supplemented with 10% FBS at 37° C. in an atmosphere of 5% $CO_2$ in air. The tumor cells were routinely subcultured three times weekly. The cells that grew in an exponential growth phase were harvested and counted for tumor inoculation.

Tumor Inoculation:

Mice (female, 6-8 weeks old) were inoculated subcutaneously at the right flank with the tumor cells (H22, EMT-6, or CT-26) in 0.1 mL PBS for tumor development. When the tumor volume reached approximately 60-80 mm³, the mice were grouped randomly according to the animal body weight and tumor volume. Each group had 5-8 tumor-bearing mice.

Observations

At the time of routine monitoring, the animals were checked for any effects of tumor growth and treatment on normal behavior such as mobility, food and water consumption (by observation only), and body weight gain/loss (body weights were measured three times weekly), eye/hair matting and any other abnormal effects. Death and observed clinical signs were recorded on the basis of the numbers of animals within each subset.

Tumor Measurements and the Endpoints

The major endpoint was to determine if tumor growth could be delayed or mice could be cured. Tumor volume was measured three times weekly in two dimensions using a caliper, and the volume was expressed in mm³ using the formula: $V = 0.5 \, a \times b^2$, where a and b are the long and short diameters of the tumor, respectively. The T/C value (in percent) was an indication of antitumor effectiveness, where T and C were the mean volume of the treated and control groups, respectively, on a given day. The T-C value was calculated according to TV. T-C was calculated with T as the median time (in days) required for the treatment group tumors to reach a predetermined size (e.g., TV as 1000 mm³), and C as the median time (in days) for the control group tumors to reach the same size. The body weights were measured and recorded at the same time to observe the toxicity of the compounds. The animals were sacrificed at the termination of the study.

Statistical Analysis

Summary statistics, including mean and the standard error of the mean (SEM), are provided for the tumor volume of each group at each time point. A two-way analysis of variance (ANOVA) was performed to compare body weight, tumor volume and tumor volume change. A one-way ANOVA was performed to compare tumor weight. All data were analyzed using GraphPad Prism 5. $p<0.05$ was considered to be statistically significant.

Example 3: Cell Proliferation Assay of Amperozide and Nepicastat in H22 Murine Hepatocarcinoma Cell Line The anti-proliferative activity of amperozide, nepicastat, and paclitaxel was tested in the H22 murine hepatocarcinoma cell line according to the experimental procedure described in Example 1. The results are shown in Table 1.

As shown in Table 1, paclitaxel showed a strong inhibition effect on H22 murine hepatocarcinoma cell line at concentrations of 1 µM and 0.1 Amperozide and nepicastat did not show any significant anti-proliferative effects on the H22 murine hepatocarcinoma cell line at these same concentrations, indicating that these two compounds are non-cytotoxic.

TABLE 1

In vitro anti-proliferation assay of Paclitaxel, Amperozide and Nepicastat in H22 murine hepatocarcinoma cell line

| Compounds | Concentration | Treatment Time | Cell viability (%) |
|---|---|---|---|
| Paclitaxel | 1 µM | 72 h | 20.8 |
| | 0.1 µM | 72 h | 28.4 |
| Amperozide | 1 µM | 72 h | 95.1 |
| | 0.1 µM | 72 h | 100.5 |
| Nepicastat | 1 µM | 72 h | 94.4 |
| | 0.1 µM | 72 h | 101.7 |
| | 0.1 µM | 72 h | 103.2 |

Figure 1:
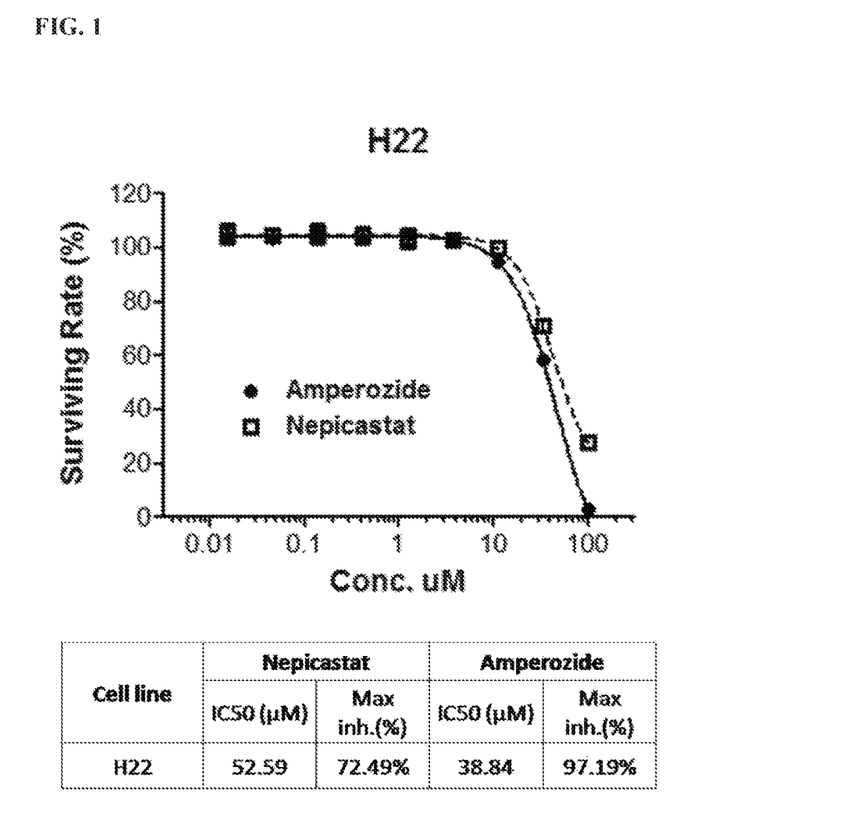
FIG. 1 shows the $IC_{50}$ data of amperozide and nepicastat in H22 murine hepatocarcinoma cells determined by the cell proliferation assay as described in Example 3.

The data are shown in FIG. 1, from which the $IC_{50}$ of amperozide and nepicastat in H22 murine hepatocarcinoma cells proliferation was calculated as 38.84 µM and 52.59 µM, respectively. It has been reported that the plasma maximal concentration ($C_{max}$) under clinical dosage of amperozide (10 mg/day) [57] and nepicastat (160 mg/day) [58] are about 0.1 µM and 0.2 µM, respectively. The $C_{max}$ values of amperozide and nepicastat at clinical dosage are much less than their $IC_{50}$ values of H22 murine hepatocarcinoma cell proliferation, suggesting that both amperozide and nepicastat are non-cytotoxic at concentrations effective to inhibit tumor growth.

The above results demonstrate that amperozide and nepicastat are non-cytotoxic in the murine H22 hepatocarcinoma cell line.

Example 4: In Vivo Anti-Cancer Activity of Amperozide and Nepicastat in Murine Model of Hepatic Cancer The anti-cancer activity of amperozide and nepicastat was evaluated in a H22 murine hepatic cancer xenograft model according to the experimental procedure described in Example 2. Anti-cancer activity was evaluated by measuring changes in tumor volume.

Figure 2A:
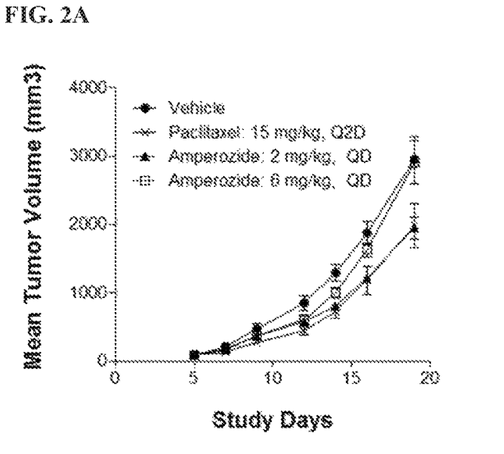
FIG. 2A shows the changes in tumor volume.
Figure 2B:
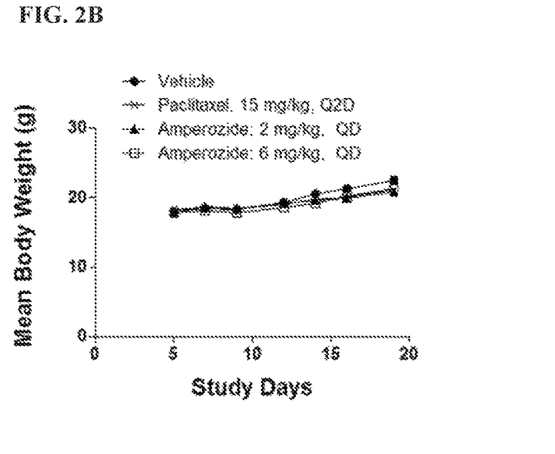
FIG. 2B shows the changes in body weight.
Figure 3A:
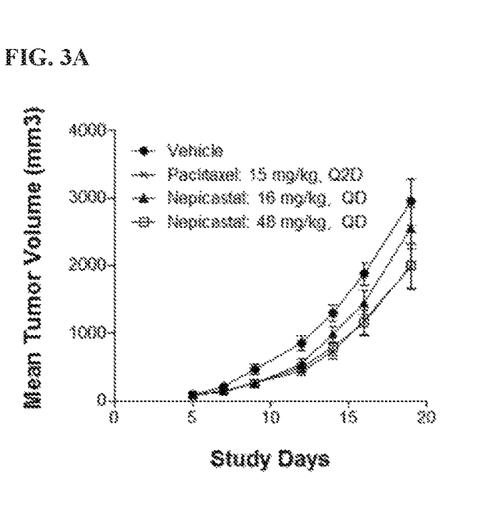
FIG. 3A shows the changes in tumor volume.
Figure 3B:
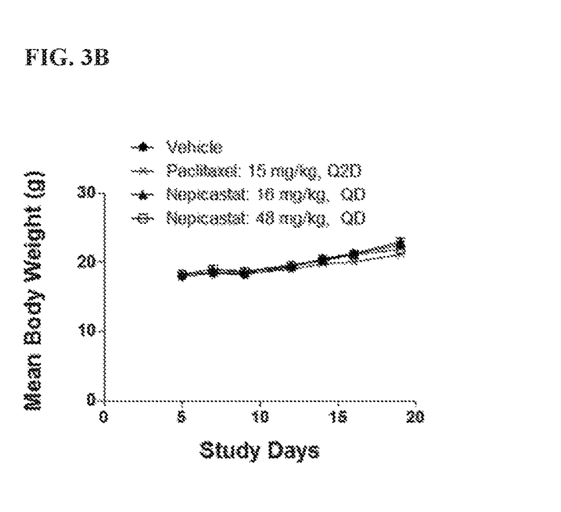
FIG. 3B shows the changes in body weight.

The results of tumor volume changes in all treatment groups at different time points after tumor inoculation are shown in Table 2. The data representing tumor growth and body weight changes for amperozide are shown in FIGS. 2A and 2B, respectively; and those of nepicastat are shown in FIGS. 3A and 3B, respectively. Table 3 summarizes the activities of amperozide and nepicastat in inhibiting the in vivo growth of H22 tumor. On day 19, the average tumor volume of vehicle group reached 3027 mm$^3$. The positive control paclitaxel showed an anti-tumor effect in the study, with the average tumor volume being 1982 mm$^3$ (T/C=65.5%, tumor growth inhibition rate=34.5%, p<0.001), indicating a successful establishment of tumor model. The average tumor volumes in the amperozide (2 mg/kg) and nepicastat (48 mg/kg) groups were 1948 mm$^3$ (T/C=64.4%, tumor growth inhibition rate=35.6%, p<0.001) and 1992 mm$^3$ (T/C=66%, tumor growth inhibition rate=34.2%, p<0.001), respectively.

cytotoxic effects as paclitaxel, as evidenced by the results of the in vitro anti-proliferation assay described in Example 3 above.

Example 5: In Vivo Anti-Cancer Activity of Nepicastat and Etamicastat Compared with Anti-PD-1 Monoclonal Antibody in a Murine Model of Hepatic Cancer The anti-cancer activity of nepicastat, etamicastat and anti-PD-1 monoclonal antibody (mAb) was evaluated in a H22 murine hepatic cancer xenograft model according to the experimental procedure described in Example 2.

Figure 4A:
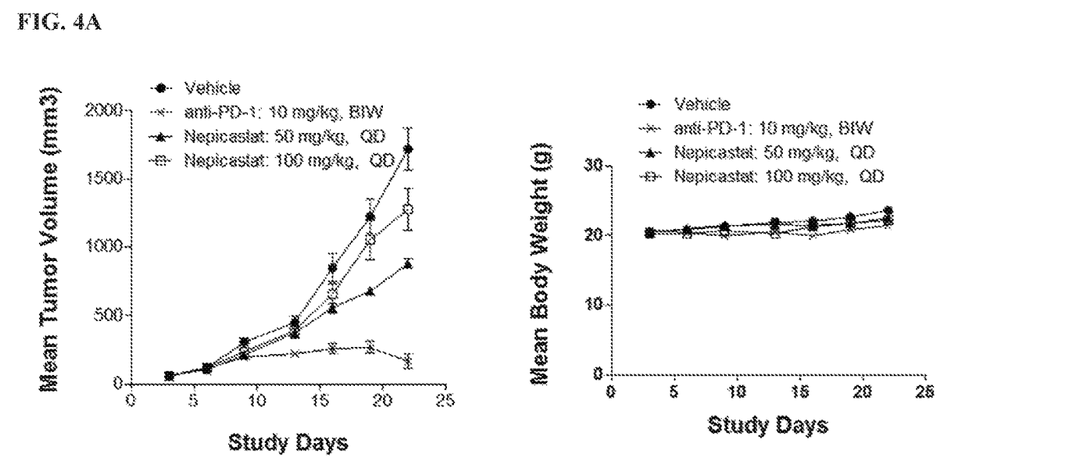
FIG. 4A shows changes in tumor volume and body weight from nepicastat treatment.
Figure 4B:
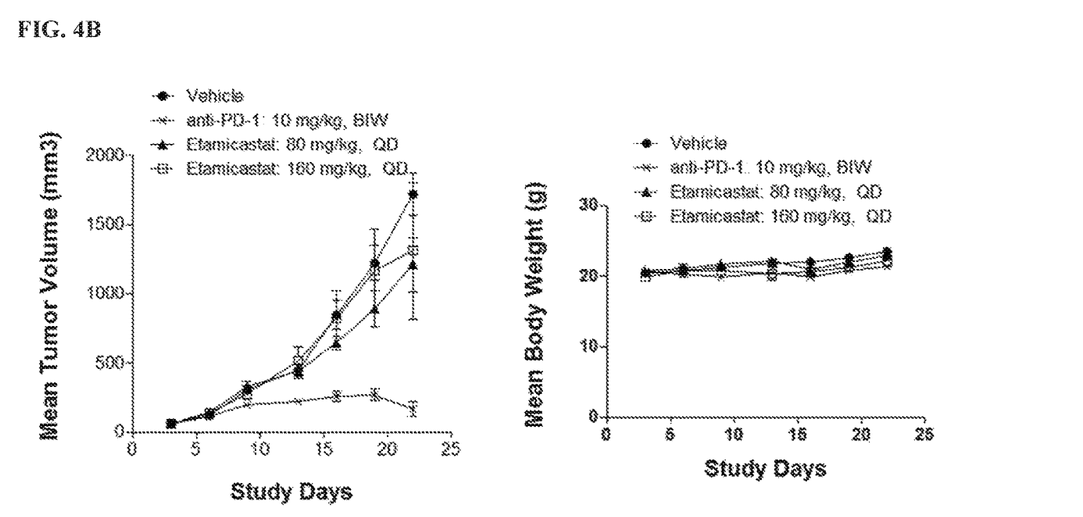
FIG. 4B shows changes in tumor volume and body weight from etamicastat treatment.

The results of tumor volume changes in all treatment groups at different time points after tumor inoculation are shown in Table 4. The data representing tumor growth and body weight changes by nepicastat and etamicastat treatment are shown in FIGS. 4A and 4B, respectively. Table 5 summarizes the inhibitory activity of nepicastat, etamicastat and anti-PD-1 mAb on in vivo growth of H22 hepatic tumors. On day 22, the average tumor volume of the vehicle group reached 1718.9 mm$^3$. The positive control anti-PD-1 mAb (10 mg/kg, twice-weekly (BIW)×6 doses, intraperitoneal administration (i.p.)) showed robust anti-tumor efficacy in the study, with an average tumor volume of 165.65 mm$^3$ (T/C=9.64%, tumor growth inhibition rate=90.36%, p<0.001), indicating a successful establishment of the tumor model. The average tumor volumes of 50 mg/kg and 100

TABLE 2

Tumor volume changes of H22 Murine Hepatic Cancer Xenografts treated with Amperozide and Nepicastat.

| Days | Vehicle | Paclitaxel 15 mg/kg | Amperozide 2 mg/kg | Amperozide 6 mg/kg | Nepicastat 16 mg/kg | Nepicastat 48 mg/kg |
|---|---|---|---|---|---|---|
| 5 | 80 ± 8 | 80 ± 9 | 80 ± 9 | 80 ± 9 | 80 ± 6 | 80 ± 6 |
| 7 | 205 ± 30 | 140 ± 17 | 166 ± 19 | 174 ± 26 | 140 ± 13 | 146 ± 12 |
| 9 | 472 ± 77 | 270 ± 48 | 355 ± 36 | 367 ± 51 | 260 ± 25 | 249 ± 26 |
| 12 | 850 ± 103 | 435 ± 60 | 576 ± 48 | 602 ± 77 | 542 ± 75 | 493 ± 74 |
| 14 | 1,294 ± 122 | 722 ± 105 | 806 ± 31 | 1,004 ± 75 | 982 ± 111 | 795 ± 129 |
| 16 | 1,878 ± 166 | 1,188 ± 206 | 1,219 ± 39 | 1,625 ± 101 | 1,454 ± 173 | 1,150 ± 188 |
| 19 | 3,027 ± 328 | 1,982 ± 327 | 1,948 ± 158 | 2,903 ± 315 | 2,546 ± 306 | 1,992 ± 349 |

TABLE 3

Antitumor Activity of Amperozide and Nepicastat in the Treatment of H22 Murine Hepatic Cancer Xenografts

| Group | Tumor Volume (mm$^3$)[a] Day 5 | Tumor Volume (mm$^3$)[a] Day 19 | T-C (days) (Reach 1000 mm$^3$) | T/C[a] (%) | TGI[b] (%) | p value |
|---|---|---|---|---|---|---|
| Vehicle | 80 ± 8 | 3,027 ± 328 | — | 100 | — | — |
| Paclitaxel (15 mg/kg) | 80 ± 9 | 1,982 ± 327 | 2 | 65.5 | 34.5 | *** |
| Amperozide (2 mg/kg) | 80 ± 9 | 1,948 ± 158 | 2 | 64.4 | 35.6 | *** |
| Amperozide (6 mg/kg) | 80 ± 9 | 2,903 ± 315 | 1 | 95.9 | 4.1 | ns |
| Nepicastat (16 mg/kg) | 80 ± 6 | 2,546 ± 306 | 1 | 84.1 | 15.9 | ns |
| Nepicastat (48 mg/kg) | 80 ± 6 | 1,992 ± 349 | 2 | 65.8 | 34.2 | *** |

[a] "T/C" refers to (mean tumor volume of test group)/(mean tumor volume of control (vehicle) group);
[b] "TGI" refers to tumor growth inhibition;
ns: not significant
*p < 0.05;
**p < 0.01;
***p < 0.001 vs. Vehicle The above results indicate that amperozide and nepicastat had similar tumor inhibition activities as paclitaxel. However, amperozide and nepicastat did not have the same mg/kg of nepicastat (once-daily (QD)×20 days, orally administered (p.o.)) treatment groups were 880.28 mm$^3$ (T/C=51.21%, tumor growth inhibition rate=48.79%, p<0.001) and 1275.47 mm³ (T/C=74.20%, tumor growth inhibition rate=25.80%, p<0.001), respectively. The average tumor volumes of 80 mg/kg and 160 mg/kg of etamicastat (Once-Daily (QD)×20 days, orally administered (p.o.).) treatment groups were 1,210.52 mm³ (T/C=70.42%, tumor growth inhibition rate=29.58%, p<0.05) and 1,309.12 mm³ (T/C=76.16%, tumor growth inhibition rate=23.84%, p>0.05), respectively.

TABLE 4

Tumor volume changes of H22 Murine Hepatic Cancer Xenografts treated with Nepicastat, Etamicastat, and anti-PD-1 mAh.

| | | Tumor Volume (mm³) | | | | |
|---|---|---|---|---|---|---|
| Days | Vehicle | anti-PD-1: 10 mg/kg, BIW | Nepicastat: 50 mg/kg, QD | Nepicastat: 100 mg/kg, QD | Etamicastat: 80 mg/kg, QD | Etamicastat: 160 mg/kg, QD |
| 3 | 56.45 ± 4.23 | 56.39 ± 3.63 | 56.45 ± 4.42 | 56.41 ± 3.96 | 56.40 ± 4.21 | 56.42 ± 3.25 |
| 6 | 119.81 ± 5.85 | 109.64 ± 6.07 | 107.64 ± 2.13 | 120.60 ± 12.92 | 142.74 ± 14.75 | 134.64 ± 14.18 |
| 9 | 307.16 ± 29.85 | 198.36 ± 26.18 | 212.98 ± 15.54 | 238.00 ± 22.62 | 325.41 ± 39.55 | 270.71 ± 33.96 |
| 13 | 447.13 ± 47.34 | 222.90 ± 29.23 | 369.64 ± 18.63 | 384.72 ± 54.05 | 437.62 ± 48.77 | 513.74 ± 103.91 |
| 16 | 847.34 ± 103.12 | 255.78 ± 36.19 | 552.37 ± 34.69 | 658.54 ± 71.96 | 645.29 ± 50.41 | 825.29 ± 198.51 |
| 19 | 1223.96 ± 128.00 | 266.89 ± 41.35 | 677.68 ± 29.38 | 1049.88 ± 145.91 | 892.56 ± 131.83 | 1167.51 ± 300.84 |
| 22 | 1718.90 ± 154.04 | 165.65 ± 53.89 | 880.28 ± 33.41 | 1275.47 ± 154.93 | 1210.52 ± 197.23 | 1309.12 ± 492.02 |

TABLE 5

Antitumor Activity of Nepicastat, Etamicastat, and anti-PD-1 mAb in the Treatment of H22 Murine Hepatic Cancer Xenografts

| Group | Tumor Volume (mm3) | | T/C$^a$ (%) | TGI$^b$ (%) | p value |
|---|---|---|---|---|---|
| | Day 3 | Day 22 | | | |
| Vehicle | 56.45 ± 4.23 | 1718.90 ± 154.04 | | | |
| anti-PD-1: 10 mg/kg, BIW | 56.39 ± 3.63 | 165.65 ± 53.89 | 9.64 | 90.36 | <0.001 |
| Nepicastat: 50 mg/kg, QD | 56.45 ± 4.42 | 880.28 ± 33.41 | 51.21 | 48.79 | <0.001 |
| Nepicastat: 100 mg/kg, QD | 56.41 ± 3.96 | 1275.47 ± 154.93 | 74.20 | 25.80 | <0.001 |
| Etamicastat: 80 mg/kg, QD | 56.40 ± 4.21 | 1210.52 ± 197.23 | 70.42 | 29.58 | <0.05 |
| Etamicastat: 160 mg/kg, QD | 56.42 ± 3.25 | 1309.12 ± 492.02 | 76.16 | 23.84 | >0.05 |

$^a$"T/C" refers to (mean tumor volume of test group)/(mean tumor volume of control (vehicle) group);
$^b$"TGI" refers to tumor growth inhibition;
ns: not significant
*p < 0.05;
**p < 0.01;
***p < 0.001 vs. Vehicle The above results confirm the anti-tumor inhibitory activity of nepicastat and etamicastat in an in vivo H22 hepatic cancer model.

Example 6: In Vivo Anti-Cancer Activity of Nepicastat in CT-26 Murine Colon Cancer and EMT-6 Murine Breast Cancer Xenograft Models Nepicastat was also tested for in vivo tumor growth inhibition in CT-26 murine colon cancer and EMT-6 murine breast cancer xenograft models. Nepicastat was administered orally.

Figure 5A:
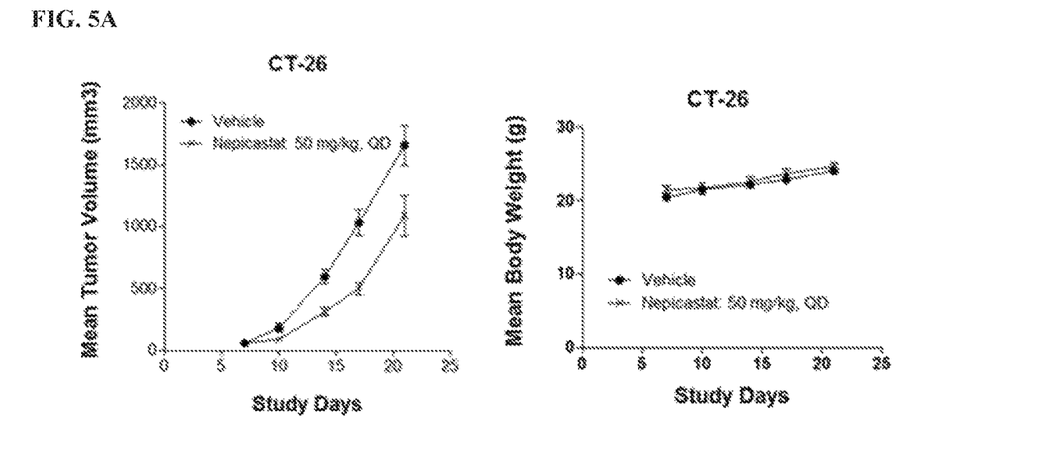
FIG. 5A shows the effects of nepicastat treatment on tumor volume and body weight in a CT-26 murine colon cancer xenograft model.
Figure 5B:
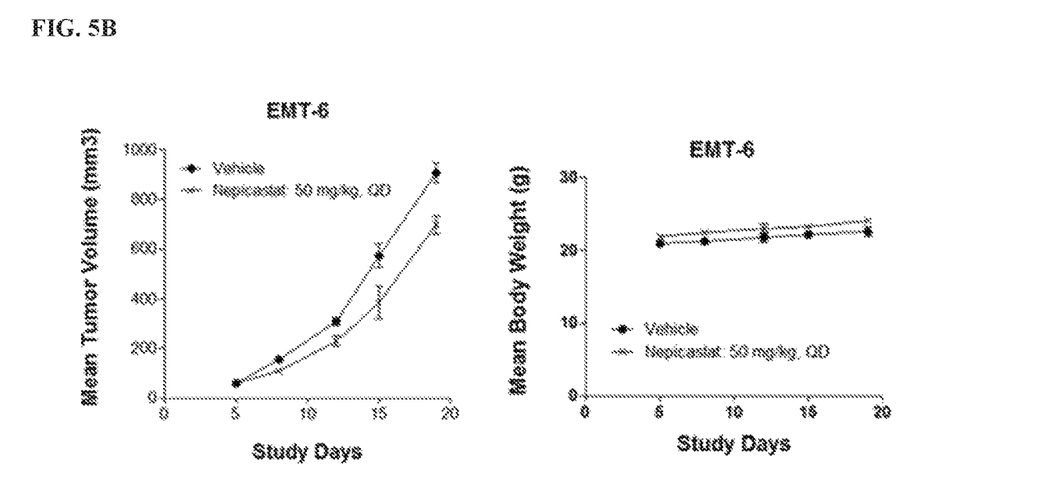
FIG. 5B shows the effects of nepicastat treatment on tumor volume and body weight in an EMT-6 murine breast cancer xenograft model.

The results of oral administration of nepicastat on tumor growth inhibition and body weight changes in the CT-26 murine colon cancer xenograft model are shown in FIG. 5A. The results of oral administration of nepicastat on tumor growth inhibition and body weight changes in the EMT-6 murine breast cancer xenograft model are shown in FIG. 5B. The data showing tumor volume changes for each indicated treatment group at different time points after tumor inoculation are shown in Table 6 (5 mice/group). Table 7 summarizes the anti-tumor inhibitory efficacy of nepicastat in CT-26 and EMT-6 murine tumor models. The group orally administered 50 mg/kg of nepicastat (once-daily (QD)) showed a tumor inhibition rate of 34.30% (p<0.001) and 23.09% (p<0.001) in CT2-6 and EMT-6 models, respectively.

TABLE 6

Tumor volume changes of CT-26 and EMT-6 xenografts treated with nepicastat.

| | Tumor Volume (mm³) in CT-26 Model | | | Tumor Volume (mm³) in EMT-6 Model | |
|---|---|---|---|---|---|
| Days | Vehicle | Nepicastat: 50 mg/kg, QD | Days | Vehicle | Nepicastat: 50 mg/kg, QD |
| 7 | 59.32 ± 1.74 | 59.35 ± 1.65 | 5 | 61.57 ± 0.83 | 61.55 ± 1.37 |
| 10 | 184.60 ± 31.57 | 86.00 ± 11.91 | 8 | 156.56 ± 8.81 | 110.11 ± 2.13 |

TABLE 6-continued

Tumor volume changes of CT-26 and EMT-6 xenografts treated with nepicastat.

| | Tumor Volume (mm³) in CT-26 Model | | | Tumor Volume (mm³) in EMT-6 Model | |
|---|---|---|---|---|---|
| Days | Vehicle | Nepicastat: 50 mg/kg, QD | Days | Vehicle | Nepicastat: 50 mg/kg, QD |
| 14 | 595.77 ± 58.92 | 314.14 ± 33.19 | 12 | 307.79 ± 15.68 | 229.32 ± 21.67 |
| 17 | 1033.04 ± 103.22 | 501.46 ± 50.04 | 15 | 573.19 ± 47.13 | 385.24 ± 66.33 |
| 21 | 1655.61 ± 160.95 | 1087.75 ± 163.63 | 19 | 906.52 ± 40.57 | 697.23 ± 35.90 |

TABLE 7

Antitumor Activity of Nepicastat treatment in CT-26 and EMT-6 xenografts

| Model | Group | Tumor Volume (mm³) Initiation | Tumor Volume (mm³) End | T/C$^a$ (%) | TGI$^b$ (%) | p value |
|---|---|---|---|---|---|---|
| CT-26 | Vehicle | 59.32 ± 3.89 | 1655.61 ± 160.95 | 65.70 | 34.30 | <0.001 |
| | Nepicastat: 50 mg/kg, QD | 59.35 ± 3.69 | 1087.75 ± 163.63 | | | |
| EMT-6 | Vehicle | 61.57 ± 1.86 | 906.52 ± 40.57 | 76.91 | 23.09 | <0.001 |
| | Nepicastat: 50 mg/kg, QD | 61.55 ± 3.06 | 697.23 ± 35.90 | | | |

$^a$"T/C" refers to (mean tumor volume of test group)/(mean tumor volume of control (vehicle) group);
$^b$"TGI" refers to tumor growth inhibition;
ns: not significant
*p < 0.05;
**p < 0.01;
***p < 0.001 vs. Vehicle The above results indicate that nepicastat also has antitumor inhibitory effects against colon cancer and breast cancer.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES

1. Rush R A and Geffen L B. Dopamine beta-hydroxylase in health and disease. *Critical Reviews in Clinical Laboratory Sciences* 1980; 12 (3): 241-77.
2. Glennon R A. Phenylisopropylamine stimulants: amphetamine-related agents. in Lemke T L, Williams D A, Roche V F, Zito W. Foye's *Principles of Medicinal Chemistry* (7th ed.). Philadelphia, USA: Wolters Kluwer Health/Lippincott Williams & Wilkins. 2013; pp. 646-648. ISBN 9781609133450.
3. Taylor K B. Dopamine-beta-hydroxylase. Stereochemical course of the reaction. *J. Biol. Chem.* 1974; 249 (2): 454-458.
4. Horwitz D, Alexander R W, Lovenberg W, and Keiser H R. Human serum dopamine-β-hydroxylase. Relationship to hypertension and sympathetic activity. *Circ. Res.* 1973; 32 (5): 594-599.
5. Mutschler J, Abbruzzese E, Witt S H, Dirican G, Nieratschker V, Frank J, et al. Functional polymorphism of the dopamine β-hydroxylase gene is associated with increased risk of disulfiram-induced adverse effects in alcohol-dependent patients. *Journal of Clinical Psychopharmacology* 2012; 32 (4): 578-80.
6. Ella E, Sato N, Nishizawa D, Kageyama S, Yamada H, et al. Association between dopamine beta hydroxylase rs5320 polymorphism and smoking behaviour in elderly Japanese. *Journal of Human Genetics* 2012; 57 (6): 385-90
7. Bhaduri N, Sinha S, Chattopadhyay A, Gangopadhyay P K, Singh M, and Mukhopadhyay K K. Analysis of polymorphisms in the dopamine beta hydroxylase gene: association with attention deficit hyperactivity disorder in Indian children. *Indian Pediatrics* 2005; 42 (2): 123-9.
8. Cubells J F, Sun X, Li W, Bonsall R W, McGrath J A, Avramopoulos D, . . . , Elston R C. Linkage analysis of plasma dopamine β-hydroxylase activity in families of patients with schizophrenia. *Human Genetics* 2011; 130 (5): 635-43.
9. Combarros O, Warden D R, Hammond N, Cortina-Borja M, Belbin O, Lehmann M G et al. The dopamine β-hydroxylase-1021C/T polymorphism is associated with the risk of Alzheimer's disease in the Epistasis Project. *BMC Medical Genetics* 2010; 11 (161): 162.
10. Goldstein M, Anagnoste B, Lauber E, and Mckeregham M R. Inhibition of dopamine-beta-hydroxylase by disulfiram. *Life Sciences* 1964; 3 (7): 763-7.
11. Goldstein M, Lauber E, and Mckereghan M R. The inhibition of dopamine-beta-hydroxylase by tropolone and other chelating agents. *Biochemical Pharmacology* 1964; 13 (7): 1103-6.
12. Stanley W C, Li B, Bonhaus D W, Johnson L G, Lee K, Porter S, et al. Catecholamine modulatory effects of nepicastat (RS-25560-197), a novel, potent and selective inhibitor of dopamine-beta-hydroxylase. *British Journal of Pharmacology* 1997; 121 (8): 1803-9.
13. Beliaev A, Learmonth D A, and Soares-da-Silva P. Synthesis and biological evaluation of novel, peripherally selective chromanylimidazolethione-based inhibitors of dopamine beta-hydroxylase. *J Med Chem.* 2006; 49(3): 1191-7.

14. Cvek B. and Dvorak Z. Targeting of Nuclear Factor-κB and Proteasome by Dithiocarbamate Complexes with Metals. *Current Pharmaceutical Design* 2007; 13 (30): 3155-67.
15. Wickström M, Danielsson K, Rickardson L, Gullbo J, Nygren P, Isaksson A, et al. Pharmacological profiling of disulfiram using human tumor cell lines and human tumor cells from patients. *Biochemical Pharmacology* 2007; 73 (1): 25-33.
16. Schweizer M T1, Lin J, Blackford A, Bardia A, King S, Armstrong A J, et al. Pharmacodynamic study of disulfiram in men with non-metastatic recurrent prostate cancer. *Prostate Cancer Prostatic Dis.* 2013; 16(4): 357-61.
17. Huang J, Campian J L, Gujar A D, Tran D D, Lockhart A C, et al. A phase I study to repurpose disulfiram in combination with temozolomide to treat newly diagnosed glioblastoma after chemoradiotherapy. *J Neurooncol.* 2016; 128(2):259-66.
18. Nechushtan H, Hamamreh Y, Nidal S, Gotfried M, Baron A, Shalev Y I, et al. A phase IIb trial assessing the addition of disulfiram to chemotherapy for the treatment of metastatic non-small cell lung cancer. *Oncologist.* 2015; 20(4): 366-7.
19. Verma S, Stewart D J, Maroun J A, Nair R C. A randomized phase II study of cisplatin alone versus cisplatin plus disulfiram. *Am J ClinOncol.* 1990; 13(2):119-24.
20. Kontoghiorghes G J, Piga A, and Hoffbrand A V. Cytotoxic and DNA-inhibitory effects of iron chelators on human leukaemic cell lines. *Hematol. Oncol.* 1986; 4(3): 195-204.
21. Ononye S N, VanHeyst M D, Oblak E Z, Zhou W, Ammar M, Anderson A C, and Wright D L. Tropolones as lead-like natural products: the development of potent and selective histone deacetylase inhibitors. *ACS Med Chem Lett.* 2013; 4(8):757-61.
22. Cook E H, Fletcher K E, Wainwright M, Marks N, Yan S Y, and Leventhal B L. Primary structure of the human platelet serotonin 5-HT2A receptor: identify with frontal cortex serotonin 5-HT2A receptor. *Journal of Neurochemistry* 1994; 63(2): 465-9.
23. Martin P, Waters N, Schmidt C J, Carlsson A, and Carlsson M L. Rodent data and general hypothesis: antipsychotic action exerted through 5-HT2A receptor antagonism is dependent on increased serotonergic tone. *Journal of Neural Transmission* 1998; 105(4-5): 365-96.
24. Aghajanian G K, Marek G J. Serotonin, via 5-HT2A receptors, increases EPSCs in layer V pyramidal cells of prefrontal cortex by an asynchronous mode of glutamate release. *Brain Research* 1999; 825(1-2): 161-71.
25. Marek G J, Wright R A, Gewirtz J C, and Schoepp D D (2001). A major role for thalamocortical afferents in serotonergic hallucinogen receptor function in the rat neocortex. *Neuroscience* 2001; 105(2): 379-92.
26. Bortolozzi A, Diaz-Mataix L, Scorza M C, Celada P, and Artigas F. The activation of 5-HT receptors in prefrontal cortex enhances dopaminergic activity. *Journal of Neurochemistry* 2005; 95(6): 1597-607.
27. Amargós-Bosch M, Bortolozzi A, Puig M V, Serrats J, Adell A, Celada P, Toth M, Mengod G, Artigas F (March 2004). "Co-expression and in vivo interaction of serotonin1A and serotonin2A receptors in pyramidal neurons of prefrontal cortex". *Cerebral Cortex* 14 (3): 281-99. doi:10.1093/cercor/bhg128. PMID 14754868.
28. Feng J, Cai X, Zhao J, and Yan Z. Serotonin receptors modulate GABA(A) receptor channels through activation of anchored protein kinase C in prefrontal cortical neurons. *The Journal of Neuroscience* 2001; 21(17): 6502-11.
29. Marek G J. Activation of adenosine(1) (A(1)) receptors suppresses head shakes induced by a serotonergic hallucinogen in rats. *Neuropharmacology* 2009; 56(8): 1082-7.
30. Zhang C and Marek G J. (January 2008). AMPA receptor involvement in 5-hydroxytryptamine 2A receptor-mediated pre-frontal cortical excitatory synaptic currents and DOI-induced head shakes. *Progress in Neuro-Psychopharmacology & Biological Psychiatry* 2008; 32(1): 62-71.
31. Gewirtz J C and Marek G J. (November 2000). Behavioral evidence for interactions between a hallucinogenic drug and group II metabotropic glutamate receptors. *Neuropsychopharmacology* 2000; 23(5): 569-76.
32. Marek G J and Zhang C. Activation of metabotropic glutamate 5 (mGlu5) receptors induces spontaneous excitatory synaptic currents in layer V pyramidal cells of the rat prefrontal cortex. *Neuroscience Letters* 2008; 442(3): 239-43.
33. Lambe E K, Liu R J, and Aghajanian G K. Schizophrenia, hypocretin (orexin), and the thalamocortical activating system. *Schizophrenia Bulletin* 2007; 33(6): 1284-90.
34. Liu R J and Aghajanian G K. Stress blunts serotonin- and hypocretin-evoked EPSCs in prefrontal cortex: role of corticosterone-mediated apical dendritic atrophy. *Proceedings of the National Academy of Sciences of the United States of America* 2008; 105(1): 359-64.
35. Durk T, Panther E, Müller T, Sorichter S, Ferrari D, Pizzirani C, et al. 5-Hydroxytryptamine modulates cytokine and chemokine production in LPS-primed human monocytes via stimulation of different 5-HTR subtypes. *International Immunology* 2005; 17(5): 599-606.
36. Urban J D, Clarke W P, von Zastrow M, Nichols D E, Kobilka B, Weinstein H, et al. Functional selectivity and classical concepts of quantitative pharmacology. *The Journal of Pharmacology and Experimental Therapeutics* 2007; 320(1): 1-13.
37. Harvey J A. Role of the serotonin 5-HT(2A) receptor in learning. *Learning & Memory* 2003; 10(5): 355-62.
38. Williams G V, Rao S G, and Goldman-Rakic P S. The physiological role of 5-HT2A receptors in working memory. *The Journal of Neuroscience* 2002; 22(7): 2843-54.
39. Yu B, Becnel J, Zerfaoui M, Rohatgi R, Boulares A H, and Nichols C D. Serotonin 5-hydroxytryptamine(2A) receptor activation suppresses tumor necrosis factor-alpha-induced inflammation with extraordinary potency. *The Journal of Pharmacology and Experimental Therapeutics* 2008; 327 (2): 316-23.
40. Nau F, Yu B, Martin D, Nichols C D. Serotonin 5-HT2A receptor activation blocks TNF-α mediated inflammation in vivo. *PloS One* 2013; 8 (10): e75426.
41. Van de Kar L D, Javed A, Zhang Y, Serres F, Raap D K, and Gray T S. 5-HT2A receptors stimulate ACTH, corticosterone, oxytocin, renin, and prolactin release and activate hypothalamic CRF and oxytocin-expressing cells. *The Journal of Neuroscience* 2001; 21 (10): 3572-9.
42. Zhang Y, Damjanoska K J, Carrasco G A, Dudas B, D'Souza D N, Tetzlaff J, et al. Evidence that 5-HT2A receptors in the hypothalamic paraventricular nucleus mediate neuroendocrine responses to (−)DOI. *The Journal of Neuroscience* 2002; 22 (21): 9635-42.
43. Hegde S S and Friday K F. Dopamine-beta-hydroxylase inhibition: a novel sympatho-modulatory approach for the treatment of congestive heart failure. *Current Pharmaceutical Design* 1998; 4 (6): 469-79.

44. De La Garza, R 2nd, Bubar M J, Carbone C L, Moeller F G, Newton T F, et al. Evaluation of the dopamine β-hydroxylase (DβH) inhibitor nepicastat in participants who meet criteria for cocaine use disorder. *Prog. Neuropsychopharmacol. Biol. Psychiatry.* 2015; 59:40-8.

45. Nunes T, Rocha J F, Vaz-da-Silva M, Igreja B, Wright L C, et al. Safety, tolerability, and pharmacokinetics of etamicastat, a novel dopamine-β-hydroxylase inhibitor, in a rising multiple-dose study in young healthy subjects. *Drugs in R & D* 2010; 10(4):225-242.

46. Almeida L, Nunes T, Costa R, Rocha J F, Vaz-da-Silva M, and Soares-da-Silva P. Etamicastat, a novel dopamine β-hydroxylase inhibitor: tolerability, pharmacokinetics, and pharmacodynamics in patients with hypertension. *ClinTher.* 2013; 35(12):1983-96.

47. Svartengren J andSimonsson P. Receptor binding properties of amperozide. *Pharmacology and Toxicology.* 1990; 66 Suppl 1:8-11.

48. Meltzer H Y, Zhang Y, Stockmeier C A. Effect of amperozide on rat cortical 5-HT2 and striatal and limbic dopamine D2 receptor occupancy: implications for antipsychotic action. *European Journal of Pharmacology.* 1992; 216(1):67-71.

49. Eriksson E. Amperozide, a putative anti-psychotic drug: uptake inhibition and release of dopamine in vitro in the rat brain. *Life Sciences.* 1990; 47(23):2111-7.

50. Yamamoto B K and Meltzer H Y. The effect of the atypical antipsychotic drug, amperozide, on carrier-mediated striatal dopamine release measured in vivo. *Journal of Pharmacology and Experimental Therapeutics.* 1992; 263 (1): 180-5.

51. Grenhoff J, Tung C S, Ugedo L, and Svensson T H. Effects of amperozide, a putative antipsychotic drug, on rat midbrain dopamine neurons recorded in vivo. *Pharmacology and Toxicology.* 1990; 66 Suppl 1:29-33.

52. Axelsson R, Nilsson A, Christensson E, and Björk A. Effects of amperozide in schizophrenia. An open study of a potent 5-HT2 receptor antagonist. *Psychopharmacology (Berlin).* 1991; 104(3):287-92.

53. Kyriakis S C, Martinsson K, Olsson N G, and Bjork A. Thin sow syndrome (TSS): the effect of amperozide. *British Veterinary Journal.* 1990; 146(5):463-7.

54. Kyriakis S C, Olsson N G, Martinsson K, and Björk A K. Observations on the action of amperozide: are there social influences on sow-litter productivity? Research in Veterinary Science. 1991; 51(2):169-73.

55. Papp I, Waller C, and Biro O. Practical experiences in the therapy of postweaning edema disease in piglets. *Berliner und Munchener Tierarztliche Wochenschrift.* (German) 1996; 109(10): 385-7.

56. Yan H, Zhang B, Li S, Zhao Q. A formal model for analyzing drug combination effects and its application in TNF-alpha-induced NFkappaB pathway. *BMC Syst Biol.* 2010; 4:50.

57. Axelsson R et al. Effects of amperozide in schizophrenia. An open study of a potent 5-HT2 receptor antagonist. *Psychopharmacology,* 1991, 104: 287-292.

58. De La Garza II R et al. Evaluation of the dopamine β-hydroxylase (DβH) inhibitor nepicastat in participants who meet criteria for cocaine use disorder. *Progress in Neuro-Psychopharmacology & Biological Psychiatry,* 2015, 59: 40-48.

59. Nunes T et al. Safety, Tolerability, and Pharmacokinetics of Etamicastat, a Novel Dopamine-b-Hydroxylase Inhibitor, in a Rising Multiple-Dose Study in Young Healthy Subjects. *Drugs R D.* 2010, 10 (4): 225-242.

We claim:

1. A method of treating a cancer in a subject in need thereof, the method comprising administering to the subject a pharmaceutical composition comprising a therapeutically effective amount of the dopamine beta-hydroxylase (DBH) inhibitor nepicastat, or a pharmaceutically acceptable salt thereof, and a pharmaceutically acceptable carrier, wherein the cancer is selected from the group consisting of colon cancer, breast cancer, and liver cancer, and wherein nepicastat or the pharmaceutically acceptable salt thereof is administered at a dose of about 20 mg/day to 160 mg/day.

2. The method according to claim 1, further comprising administering to the subject at least one additional anti-cancer agent selected from the group consisting of a chemotherapeutic agent, a targeted therapy agent, and an immunotherapy agent.

3. The method according to claim 1, wherein the treatment is performed in combination with at least one additional cancer therapy selected from the group consisting of surgery, gene therapy, radiotherapy, and cryotherapy.

4. The method according to claim 1, wherein the subject is a human subject.

* * * * *